(12) United States Patent
Stepanik et al.

(10) Patent No.: US 7,080,544 B2
(45) Date of Patent: Jul. 25, 2006

(54) APPARATUS SYSTEM AND METHOD FOR GAS WELL SITE MONITORING

(75) Inventors: Radim Stepanik, Red Deer (CA);
Perry Osberg, Red Deer County (CA)

(73) Assignee: Firemaster OilField Services Inc., Red Deer (CA)

( * ) Notice: Subject to any disclaimer, the term of this patent is extended or adjusted under 35 U.S.C. 154(b) by 0 days.

(21) Appl. No.: 10/603,021

(22) Filed: Jun. 25, 2003

(65) Prior Publication Data

US 2004/0075566 A1    Apr. 22, 2004

Related U.S. Application Data

(60) Provisional application No. 60/405,288, filed on Aug. 23, 2002.

(51) Int. Cl.
*G01N 31/00*    (2006.01)
*G06F 19/00*    (2006.01)

(52) U.S. Cl. ........................ 73/31.02; 702/22
(58) Field of Classification Search ............... 73/23.21, 73/31.02; 702/22
See application file for complete search history.

(56) References Cited

U.S. PATENT DOCUMENTS

| | | | | |
|---|---|---|---|---|
| 3,444,521 A | * | 5/1969 | Beese | 340/3.52 |
| 4,135,092 A | * | 1/1979 | Milly | 250/343 |
| 4,551,719 A | * | 11/1985 | Carlin et al. | 340/825.36 |
| 4,642,296 A | * | 2/1987 | Hubner | 436/138 |
| 5,132,968 A | * | 7/1992 | Cephus | 370/349 |
| 5,159,315 A | * | 10/1992 | Schultz et al. | 340/539.26 |
| 5,184,502 A | * | 2/1993 | Adams et al. | 73/31.01 |
| 5,235,633 A | * | 8/1993 | Dennison et al. | 455/456.3 |
| 5,281,816 A | * | 1/1994 | Jacobson et al. | 250/339.05 |
| 5,363,093 A | * | 11/1994 | Williams et al. | 340/605 |
| 5,406,265 A | * | 4/1995 | Trozzo et al. | 340/632 |
| 5,553,094 A | * | 9/1996 | Johnson et al. | 375/130 |
| 5,568,121 A | * | 10/1996 | Lamensdorf | 340/539.17 |
| 5,650,770 A | * | 7/1997 | Schlager et al. | 340/573.1 |
| 5,805,813 A | * | 9/1998 | Schweitzer, III | 709/217 |
| 6,104,229 A | * | 8/2000 | Lien | 327/434 |

(Continued)

FOREIGN PATENT DOCUMENTS

GB        2273593 A    *  6/1994

*Primary Examiner*—Hezron Williams
*Assistant Examiner*—John Fitzgerald
(74) *Attorney, Agent, or Firm*—Hicks & Associates; Andrew Hicks

(57) ABSTRACT

A System and a Method of initializing and using that system are described in various embodiments all suitable for use remotely monitoring gas escapes on oil or gas well-sites, particularly as early warning technologies for use in preventing injury to workers or populations adjacent those well-sites. The system efficiently uses the Internet to securely transmit pre-processed data off-site for a range of different uses either directly to well-site operators or via a server for value-added handling of and convenient access by operators and others to information based on the data. The system conserves both IP addresses and communications bandwidth without compromising access to detailed data respecting well-site status. The novel system includes means for using multiple modes of long-distance communications technology that can be configured manually or that conveniently auto-senses and auto-selects the appropriate communications mode to use for transmitting data off-site via the Internet according to the location of installation of the system and whether or not it has entered an alarm condition.

10 Claims, 10 Drawing Sheets

U.S. PATENT DOCUMENTS

| | | | |
|---|---|---|---|
| 6,114,946 A * | 9/2000 | Michels | 340/146.2 |
| 6,169,488 B1 * | 1/2001 | Ketler | 340/632 |
| 6,252,510 B1 * | 6/2001 | Dungan | 340/632 |
| 6,259,956 B1 * | 7/2001 | Myers et al. | 700/80 |
| 6,317,029 B1 * | 11/2001 | Fleeter | 340/10.32 |
| 6,369,715 B1 * | 4/2002 | Bennett et al. | 340/618 |
| 6,405,135 B1 * | 6/2002 | Adriany et al. | 702/5 |
| 6,415,646 B1 * | 7/2002 | Kessel et al. | 73/23.2 |
| 6,490,530 B1 * | 12/2002 | Wyatt | 702/24 |
| 6,701,772 B1 * | 3/2004 | Kreichauf et al. | 73/23.2 |
| 6,701,776 B1 * | 3/2004 | Stetter | 73/49.2 |
| 6,770,887 B1 * | 8/2004 | Krivanek et al. | 250/396 R |
| 6,794,991 B1 * | 9/2004 | Dungan | 340/632 |
| 6,946,671 B1 * | 9/2005 | Smith et al. | 250/559.4 |
| 7,006,923 B1 * | 2/2006 | Rubin | 702/19 |
| 2001/0040509 A1 | 11/2001 | Dungan et al. | |
| 2002/0155622 A1 | 10/2002 | Slater et al. | |
| 2002/0163579 A1 * | 11/2002 | Patel et al. | 348/207.1 |
| 2003/0149526 A1 * | 8/2003 | Zhou et al. | 701/213 |

* cited by examiner

APPARATUS SYSTEM AND METHOD FOR GAS WELL SITE MONITORING

RELATED APPLICATIONS

This application claims the benefit of U.S. Provisional Application No. 60/405288 filed 23 Aug. 2002.

FIELD OF THE INVENTION

The present invention relates generally to gas well safety and particularly to early warning technologies for use in preventing injury to workers and populations adjacent gas well sites.

BACKGROUND OF THE INVENTION

Exploring and producing natural gas and crude oil has a whole variety of hazards. Flammable gas will be continually present during the processes involved requiring that plant and personnel be monitored for risk levels. Gas well sites are hazardous in a number of ways to both site workers and adjacent properties. Critical Leases are well sites that include a (significant) risk of escape of poisonous or explosive vapours "On Lease", typically in specific "critical zones" (also known as Hot Zones) separate from a work area or "Job Shack" from which workers monitor the entire well site. "Downwind" from such critical leases, poisonous vapours (an indicator of which is the combustion product generated during flaring activities) threaten nearby humans and livestock to different extents influenced by wind direction and speed. Geologists provide information respecting the location of "sour zones" such that for new wells Drilling Rig operators in cooperation with a Drilling Consultant will determine where to place Stationary Monitoring Units (SMUs) both On Lease and Downwind. Similarly, during the production phase of an existing well, Service Rig operators in cooperation with a Drilling Consultant will determine how to setup "forehead monitoring" and downwind equipment.

The Lower Explosive Limit (LEL) of a flammable gas is the minimum concentration of that gas, at normal ambient conditions, at which it will burn if there is a source of ignition present. At a concentration below the LEL, the gas will not burn. Gas detectors for flammable gases are typically calibrated in the range 0–100% LEL. The actual concentration of the LEL varies from one gas to another. It has become industry practice that workers not enter spaces where the concentration of a gas exceeds 20% of the LEL because the concentration will vary at different places and it is likely that there will be pockets of gas that will exceed the LEL creating risk of explosion such that it is important to monitor LEL levels on such work sites. Further, various regulatory bodies impose monitoring requirements on lease requiring well site operators to track the percentage of the LEL of various flammable gases present on site.

Conventional technologies for "On Lease" monitoring provide relatively local audible and visual alarms that alert workers in the Job Shack, who must then "suit up" in chemical proof garments before approaching the hot zones to determine which of a plurality of such zones has entered alarm condition. Disadvantageously, the need to suit up creates delay in handling an emergency while the need to approach a hot zone creates (avoidable) risk to the worker. Conventional technologies for Downwind monitoring rely on a plurality of independent monitoring stations that may each communicate directly with a central monitoring station, such that a plurality of modems are deployed at significant expense for marginal benefit in redundancy.

Supervisory Control and Data Acquisition ("SCADA") systems have been used in industry to monitor and control plant status at the same time as providing records of that status or "logging" functionality. SCADA systems usually interface to the subject equipment in the plant using some form of programmable logic control ("PLC") device (useful stand-alone or in conjunction with a system to automate the monitoring and control of an industrial plant). As the name indicates, SCADA is not a full control system, but operates in a supervisory manner providing alarms that alert operators who then take manual control of the problematic equipment. SCADA is implemented as software positioned on top of the equipment to which it is interfaced using any suitable commercial hardware module. Systems similar to SCADA systems are often referred to as Distributed Control Systems (DCS), usually located within a confined area such that communication can be on a local area network (LAN) that is reliable and high speed. However, wireless Remote Terminal Units ("RTUs") can also be used to transfer to different sites the data accessed from equipment being monitored and controlled. Typically the data acquisition is by an RTU including a PLC to receive the various inputs continuously delivered at high transfer rates by equipment hardwired to the RTU. In modern SCADA systems a host or master terminal unit then periodically scans or polls one or more wireless RTUs to gather the input data so acquired. This data can be analog or digital information gathered by monitoring sensors (e.g. flowmeter, ammeter), or data that controls equipment (e.g. relays, valves, motors) automatically or with operator intervention. Conventional SCADA systems use the RTU as a high reliability buffer and relay utility that can receive relatively large volumes of data and forward it as needed for processing by a host or master unit, the benefit of which is continuous logs that may be processed and re-processed by a host in different ways to extract information for different purposes as required. As host processing power has increased the buffering functionality of the RTU has become less important making it possible for systems (such as SMART described below) to have a plurality of sensors transmitting directly to the host without an RTU. Data whether buffered or directly transferred may be processed for a variety of purposes by a SCADA system, for example, the data is typically processed by the host to detect alarm conditions, and if an alarm is present, an alarm related interface can display notice of the condition causing the alarm. Conventional RTUs forwarding sensor traffic via RF to a master unit at a plant control center typically rely on relay towers or large antenna suitable for high power transmission, which for rapid deployment applications in remote locations (e.g. undeveloped regions of the Arctic) makes them either unavailable (e.g. no supporting infrastructure) or uneconomical (e.g. too expensive to justify transport) to implement for short-term, including emergency installations.

Although no patented prior art is known to the applicant, a number of companies providing portions of the above conventional solutions have been identified, including BW Technologies whose detection and analysis technology focus is efficiency rather than safety. The Rig Rat II is a microprocessor based gas detection apparatus detecting for combustibles, toxics, and/or oxygen hazards On Lease. With independent wireless radio signal transmission via coded radio channels the independently powered, solar capable detectors are easily moved. Rig Rat II is modular in design with plug-in ports for remote sensors, remote alarms, relays, and solar power. Installation costs are reduced by the use of wireless technologies, thereby eliminating cabling, wiring, conduit and trenching. Although the Rig Rat II is intrinsically safe, permitting it to be deployed inside hot zones, it has no ability to transfer data to remote locations, through the InterNet or otherwise.

Further, SAT-TEL Corporation provides its SMART system for Downwind applications working with Iroc Systems Corp. Using Sat-Tel's SMART (Satellite Monitored Automated Reporting Terminal) monitoring technology assets are easily managed regardless of their geographic location. Sat-Tel configures existing technology to provide real-time monitoring via satellite communication. Unlike Rig Rat II, SMART is not intrinsically safe and cannot be deployed On Lease in hot zones. Like Rig Rat II, SMART units are self sufficiently powered by a 12V car battery charged via solar panel, tracking it's own power status. Designed to monitor four sensor inputs, such as humidity, weight, and wind speed. The Data Logger element of the SMART system takes samples at industry standard five second intervals, averaged every minute, and reported every fifteen minutes. Data is sent to Sat-Tel's call center via wireless fixed site satellite modem. Sat-Tel's SMART technology is specifically designed for $H_2S$ ppm, $SO_2$ ppb gas detection and is for use in only the downwind monitoring application. Further, SMART is based on proprietary MSAT communications links that support highly directional, one-way, data transmission only, making it necessary for operators to carry separate voice communication devices. SMART is characterized by unnecessary multiple redundancies in both data collection and transmission, with each unit requiring a separate MSAT satellite transponder and IP address (i.e. for each sensor station) multiplying communication costs. MSAT's reliance on static IP addressing disadvantageously creates a security risk, while its one-way configuration disadvantageously prevents remotely transmitting instructions to the equipment on a remote site. Further MSAT is not suitable for the transmission of Motion JPEG video images.

U.S. Patent Application 2001/0040509 ("509") filed by Dungan apparently teaches an apparatus and method for wireless gas monitoring, which purportedly improves over older Remote Terminal Unit ("RTU") based technology by allegedly "integrating" the transmitter in the same housing as the gas sensor or sensor array. Although not limited to satellite transmissions, in the 509 application at FIG. 4 one embodiment is disclosed according to which Low Earth Orbit ("LEO") satellite means are used to relay a signal from a Monitoring Station (14) adjacent a hazardous location to a remote Master Station (118) for further handling. Since the stated problem with the prior art RTUs is the need for "large" dish antennas having "higher gain", making it attractive to eliminate the use of "bulky and expensive" RTUs the LEO system operating at low altitude within relatively easy reach of less powerful transmitters is essential to the operation of the 509 system. Disadvantageously the LEO approach suffers from a "small footprint" limitation inherent in this low-power technology resulting in restrictions on the areas in which it may be deployed for remote access. The one-to-one transmitter-to-sensor correspondence of the 509 system is also very similar to SMART by Sat-Tel/IROC such that including the transmitter in the sensor housing is characterized by unnecessary multiple redundancies in high-powered data transmission whenever a plurality of sensors are deployed. Both 509 and SMART implement a "stand-alone" independent sensor & transmitter combination according to which each sensor or monitoring station sends data to a remote "master" (whether on-site or off-site respecting the gas detection location) that responds in some manner to the information carried in such data. Although the amount of data so transmitted can vary (e.g. normal vs. alarm mode) both 509 and SMART necessitate significant overhead in air-time for the transmission of data, when used in remote sensing applications disadvantageously resulting in the consumption of expensive (high-powered, long-distance) bandwidth during each transmission from each sensor station. Aggravating the above situation is the commensurate consumption of extra IP-addresses by the unnecessary multiple redundancy of the configuration of the 509 and SMART systems, dictating one IP address per sensor station, when equivalent information about each station may now be transmitted without consuming one IP-address per station. 509 further teaches at para. 70 a large number of very rapid sensor signal transmissions such that no averaging or pre-processing at the sensor station is permitted since "each monitoring device 14 will very rapidly transmit its readings to an output center. Because these transmissions occur so often, there is insufficient time for data readings to accumulate between transmissions.", which failure to pre-process data from sensor stations further increases the burden on the communications system and budget. It is therefore desirable to both process and transmit sensor data in a manner that reduces the amount of data sent and the communication uplink usage time—without compromising the quality or completeness of the information required to achieve the system objectives of location targeted early warning, nature and direction of gas escape, and sufficient records to comply with local regulations.

A common problem with all gas sensors, especially those operating at remote sites, is anomalous readings (false alarms) resulting from substantial shifts in temperature, wind speed, humidity or other atmospheric conditions that influence the (best) interpretation of the raw signal from sensors. It is desirable to compensate for such changes in atmospheric conditions (resulting for example from forest fires and fast moving cold fronts—common in mountainous terrain) by adjusting the interpretation of sensor data, before it is processed, by averaging unadjusted data into other data that would be distorted by its inclusion.

All known conventional well-site monitoring systems are wireless, use a 19.2 kbps data communication IP connection, and are independently powered, but are limited to either On Lease or Downwind applications and use relatively expensive and inflexible technologies. There is a need for a relatively simple and affordable integrated system that may be used in a variety of applications to communicate remotely using the InterNet efficiently transferring information regarding several sensors via a single IP address. None of the known conventional technologies temperature compensates sensor data. None of the known conventional technologies integrates video security functionality with its gas monitoring.

Schlumberger's new product currently known as "InterACT" is described as providing "secure, real-time, Web-based exploration, development and production data." InterACT allegedly permits authorized team members located anywhere around the globe to view data in the course of collaborative decision making. It is further described as suitable for: Remote data acquisition and delivery; Two-way communication and distribution of real-time drilling, wireline, stimulation and production information; Selective sharing of data among several parties; Remote monitoring of well-site operations; and Supervisory control of remote assets. Although limited information is currently available respecting how it allegedly achieves the above functionality, it is believed that in the Remote monitoring application the InterACT system uses a group of local sensor stations that transmit via RF to a relay device that forwards data via FTP to a server off-site for viewing by users. Disadvantageously, when the InterACT monitoring system is setup in an area having access to both (less expensive) cellular service and (more reliable) satellite service, the communications element has no means to auto-detect, auto-select, and auto-switch between satellite and cellular communication modes whenever and as it becomes appropriate to do so. The InterACT system also fails to provide for dual voice-IP usage of the communication system.

U.S. Patent Application 20020155622 ("622") by Slater et al. purports to teach a "toxic gas monitoring system" based on individual (slave) radio-paging units worn by workers in hazardous areas. According to one embodiment the pagers receive an alarm signal from a centrally located (master) sensor unit and transmitter, which signal warns all workers of the presence of gas in the subject work space. According to another embodiment the pagers each include a gas sensor, are self-identifying, and have 2-way communication capability including a "panic button" such that any pager can trigger the entire system into alarm. According to a third embodiment the 2-way pagers and their centrally located (master) sensor unit each communicate with an external resource such as a rescue crew. 622 contemplates a group of such systems operating in "repair cells" to cover a large industrial facility. There is no indication in 622 that much more than simple signals are exchanged over limited distances to trigger events such as alarms that alert operators and supporting resources to the presence of gas.

Industrial facilities commonly use the popular HART® protocol for which a wide array of reliable and affordable peripheral devices have been developed over years. The HART® Multiplexor system facilitates the gathering of HART® protocol data in order to permit asset management by those who operate and maintain a plant. Data is gathered via a plug-in modular unit housed on a field termination board. The multiplexor and fieldgates enable the use of a PC for the remote monitoring, remote diagnosis and remote configuration of connected HART® sensors and actuators, via telephone lines (analogue and ISDN), Ethernet TCP/IP, or mobile communications (e.g. GSM). Communication with the field device is a sub-layered service that does not interrupt the measurement signal, such that data access procedures have no influence on the measured value processing performed by associated process control and instrument systems. Consequently, it is desirable for remote access applications to have available means for connecting "off the shelf" sensors and other peripherals from which data may be gathered and which connection employs a popular and reliable industry standard.

SUMMARY OF THE INVENTION

The system aspect of the present invention is an innovative use of new and existing technology comprising a simple and affordable package functional in a variety of applications that communicate with a remotely located monitoring, control, and record keeping centre via the InterNet. By using the InterNet for the secure transmission of data from the system of the present invention either directly to users or through a server, user location flexibility and convenience is dramatically enhanced, permitting users to access data in transit and using "hotspots" without prior setup required. In order to overcome the disadvantages of the prior art a novel system for On Lease or Downwind monitoring has been created according to which hot zones are monitored remotely and adjacent properties are protected by a single communications device having a plurality of SMUs. Advantageously workers no longer need to suit up or even risk leaving a pressure positive Job Shack in order to determine the origin of an alarm generated by conventional technologies. Advantageously operators no longer need to pay for multiple IP addresses or have redundant telecommunications devices to deliver the relatively small data streams necessary to fully protect workers and adjacent properties.

The gas monitoring system of the present invention is suitable for rapid deployment in remote areas not having access to infrastructure. It uses high-powered data transfer resources (e.g. long-distance communication via satellite or cellular) efficiently and affordably by both processing and transmitting gas sensor data in a manner that reduces the communication uplink usage time—without compromising the quality or completeness of the information required to achieve the system objectives of: location targeted early warning, detailed information respecting the nature and direction of the gas escape, and sufficient records to comply with local regulations. For example, the system of the present invention requires only one IP address per sensor station group, yet provides equivalent information about each sensor station, but overcomes the disadvantage of the prior art that commonly used one IP-address per sensor station. Similarly by suitably pre-processing sensor data significant advantages are achieved in bandwidth efficiency during normal mode operation, without precluding the transmission of full sets of sensor data, when a system enters alarm mode, for later reprocessing. And the CCI element of the system of the present invention also identifies the "modem of preference" using on-board RSSI (relative signal strength indicator) detection technology to determine which modem best satisfies the rules pre-defined for the particular circumstances—all thereby reducing the burden on the communications system and budget over the life of the installation of each system.

Pre-compensating for local weather anomalies and modularly constructed from reconfigurable elements, the system of the present invention is further suitable for such rapid deployment application in easily customized packages for a particular location regardless of the changes in weather and other local factors such as intermittent access to communication with a remote call center or other monitoring facility that provides archive, user access, regulatory tracking, emergency service links and other advantageous functionality. The option for low-power transmission between sensor devices and one or more CCI (message processor) devices not only provides for an efficient use communications resources but effectively also serves to provide fail-over capacity for each CCI.

Although it is desirable for all installations, it is particularly important for remote access applications (where security is normally important and parts are difficult to obtain) that the system of the present invention contemplates and facilitates the connection of "off the shelf" sensors and other peripherals (e.g. video imaging service and HART® protocol devices) from which data may be gathered or which connection is effected using a popular and reliable industry standard.

Global Positioning System (GPS) equipment is used to locate Universal Transverse Mercator (UTM) grid readings typically specified by a regulatory body who determines how many SMUs of each type need to be deployed and where they must be placed. Once the physical site for a SMU is located, whether according to the known hot zones On Lease or via UTM readings downwind, system initialization can proceed.

In the Downwind configuration the system operator positions a SMU including a Sensor Interface Transceiver (SIT) SIT-02 (with $H_2S$ and/or $SO_2$ sensors) apparatus on a UTM and connects any common GPS measuring device to the SIT-02 (via a serial port) to confirm the accuracy of the required positioning. SMU install locations will typically be less than 1 km apart with the Command Control Interface (CCI) centrally located between SMUs to obtain maximum coverage. Since the downwind configuration of the system is never in a hot zone, there is no requirement that the CCI be intrinsically safe—permitting a less expensive housing to be used for each of the SIT-02 units and the supporting CCI. When the system is setup communications are first tested and then the sensors are tested by the application of a ("bump gas") sample of each gas that the particular sensor is designed to detect in order to verify operation in the field, all SMUs having been previously calibrated and tested under lab conditions. The CCI includes a built-in voice-capable phone (Cellular or Satellite) that permits operators to immediately verify if the correct readings are being registered at the remote call center.

Remote monitoring within the perimeter of a Critical Lease is enabled when the On Lease configuration of the system aspect of the present invention deploys a plurality of SIT-01 to relay information locally over relatively short distances from a plurality of external (gas detection and analysis) sensor units (typically the Rig Rat II) via RF (typically at 900 MHz) to a CCI that provides logging and long-distance remote (Cellular or Satellite) communication capability. Similarly, the Downwind configuration of the system of the present invention involves the local relay of information from a plurality of SIT-02 via RF to a CCI that provides long-distance remote communication capability.

In both configurations the CCI transmits via a Cellular Digital Packet Data ("CDPD") network if it is available at the site location, or in the alternative via Globalstar Qualcomm satellite link to a remote call centre where both normal and alarm data are monitored and processed. The selection (set via DIP switch) of CDPD or Satellite communications is made onboard the CCI at the time of installation when the equipment install location is known and confirmed such that it can be determined whether the less expensive cellular communication option is available. However Globalstar technology can work on CDMA cellular service and kick up to satellite when out of the cellular zone. In a preferred embodiment the Globalstar system deployed advantageously operates with a dynamic IP, which is significantly more secure against hacking.

According to one aspect of the invention there is provided a novel intrinsically safe electronic system having a central communication interface, for use with means for gas detection and analysis located on a sour gas or critical lease well site, the system comprising: a source of electrical energy; means for receiving at least one analog signal from said gas detection and analysis means for the purpose of identifying the nature and presence or concentration of at least one gas; an A/D converter for converting said at least one analog signal to a digital signal; and wireless means for transmitting said digital signal to said central communication interface for further handling, wherein said central communication interface comprises: a micro-controller having a memory stack; ROM and EEPROM; solar charging and power regulation circuitry; at least one serial bus and port; an atmospheric conditions interface for receiving sensor input respecting at least one atmospheric condition; wireless means for receiving said digital signal; means for storing and processing said digital signal for the purpose of creating and maintaining a data log respecting the nature and presence or concentration of at least one gas over varying periods of time; wireless means for transmitting said data log to a remote location; and an intrinsically safe housing. Further wherein said source of electrical energy comprises at least one battery together with solar powered means for charging said at least one battery. Further wherein said means for receiving said at least one analog signal from said gas detection and analysis means comprises a serial connection port and suitable cable. Further comprising means for detecting the percentage of the Lower Explosive Limit ("LEL") level of a flammable gas in the air on said well site. Further wherein said wireless means for transmitting said digital signals to said central communication interface comprises an intrinsically safe communications relay apparatus that operates within the Radio Frequency portion of the electromagnetic spectrum at any suitable frequency therein. Further wherein said wireless means for transmitting said data log to a remote location comprises a modem adaptable to transmitting through a Cellular Digital Packet Data network and accessing any such suitable network using internet protocol together with any suitable router or similar device in order to transfer said data log using an IP address. Further wherein said means for storing and processing said digital signal comprises a micro-controller together with a firmware module and any suitable memory means. Further wherein wherein said wireless means for transmitting said data log to a remote location comprises a satellite transponder accessing a satellite network using internet protocol together with any suitable router or similar device in order to transfer said data log using an IP address. Further comprising any suitable camera, video transmitter and video server device for capturing and compressing digital images together with suitable switching means, for transmission using said wireless means for transmitting said data log to a remote location. And, further comprising onboard voice phone communication means housed with said central communication interface.

According to one aspect of the invention there is provided a novel electronic system having a central communication interface, for use downwind from a sour gas or critical lease well site, the system comprising: a plurality of sensor interface means for gas detection and signal generation each producing at least one digital signal representing the nature and presence or concentration of at least one gas in proximity thereto; and a source of electrical energy for each said sensor interface means, wherein each said sensor interface means has wireless means for transmitting said digital signal to said central communication interface for further handling. Further wherein said sensor interface means for gas detection and signal generation comprises: a source of electrical energy; a micro-controller having embedded firmware and a memory stack; solar charging and power regulation circuitry; at least one serial bus and port; an atmospheric conditions interface for receiving sensor input respecting at least one atmospheric condition; at least one input port for connecting a gas sensor for the purpose of receiving at least one analog signal from said sensor; an A/D converter for converting said at least one analog signal to a digital signal; and wireless means for transmitting said digital signal to said central communication interface for further handling. Further wherein said central communication interface is provided with wireless means for transmitting a data log to a remote location, and said central communication interface comprises: a micro-controller having a memory stack; ROM and EEPROM; solar charging and power regulation circuitry; at least one serial bus and port; an atmospheric conditions interface for receiving sensor input respecting at least one atmospheric condition; wireless means for receiving said digital signal; means for storing and processing said digital signal for the purpose of creating and maintaining a data log respecting the nature and presence or concentration of at least one gas over varying periods of time; and onboard voice phone communications. Further wherein said source of electrical energy comprises at least one battery together with solar powered means for charging said at least one battery. Further wherein said analog signal represents the ppm of $H_2S$ or the ppb of $SO_2$ in the air downwind from said well site. Further wherein said wireless means for transmitting said digital signals to said central communication interface comprises a communications relay apparatus that operates within the Radio Frequency portion of the electromagnetic spectrum at any suitable frequency therein. Further wherein said wireless means for transmitting said data log to a remote location comprises a modem adaptable to transmitting through a Cellular Digital Packet Data network and accessing any such suitable network using internet protocol together with any suitable router or similar device in order to transfer said data log using an IP address. Further wherein said means for storing and processing said digital signal comprises a micro-controller together with a firmware module and any suitable memory means. Further wherein said wireless means for transmitting said data log to a remote location comprises a satellite transponder accessing a satellite network using internet protocol together with any suitable router or similar device in order to transfer said data log using an IP address. Further comprising any suitable camera, video transmitter and video server device for capturing and compressing digital images together with suitable switching means, for transmission using said wireless means for transmitting said data log to a remote location. Further wherein said at least one atmospheric condition comprises wind direction, wind speed, temperature, or humidity.

According to another aspect of the invention there is provided a novel method of initializing a system having a central communication interface, for use with means for gas detection and analysis, located on a critical lease well site, or for use downwind from said critical lease well site, comprising the steps: apply power to said central communication interface; verify communications between said central communication interface and all SIT units; test each SIT and sensor using bump gas means to send each sensor to alarm; physically chart the sensor readings; and use onboard voice phone means to confirm output accuracy. Further wherein said phone comprises a Globalstar transponder.

There is further provided a novel method of implementing and operating a system having a central communication interface, for use with means for gas detection and analysis, located on a critical lease well site, or for use downwind from said critical lease well site, comprising the steps: obtaining and verifying data relating to the presence of gas on lease; determining ambient atmospheric conditions, including air temperature, wind speed and direction, humidity from at least one location either On Lease at said site or Downwind from said site; adjusting (for the purpose of reducing anomalous readings) said obtained data if required to account for recent changes in said atmospheric determinations; if said data is outside preset alarm parameters, then storing said data for use in averaging said data at predetermined intervals for later transmission; or if said data is within preset alarm parameters, then entering a pre-configured mode for immediate transmission; and transmitting said data for further processing at a remote location.

According to one aspect of the invention there is provided an apparatus for accepting and converting, to digital, analog data from at least one gas sensor and wirelessly transmitting said digital data to a central communication interface, said apparatus comprising: a source of electrical energy; a sensor interface; means for receiving said raw data from sensors via said sensor interface; a sensor interpretation and signal generation firmware module; means for processing at least one signal into a digital form; and wireless means for transmitting said signal to said central communication interface. The apparatus further comprises an atmospheric conditions interface providing analog data respecting at least one atmospheric parameter such as for example, but not in limitation, temperature, wind direction, wind speed, or humidity.

The accompanying drawings, which are incorporated in and constitute a part of this specification, illustrate preferred embodiments of the method, system, and apparatus according to the invention and, together with the description, serve to explain the principles of the invention.

BRIEF DESCRIPTION OF THE DRAWINGS

The present invention, in order to be easily understood and practiced, is set out in the following non-limiting examples shown in the accompanying drawings, in which.

DETAILED DESCRIPTION OF THE PREFERRED EMBODIMENT

Figure 1:
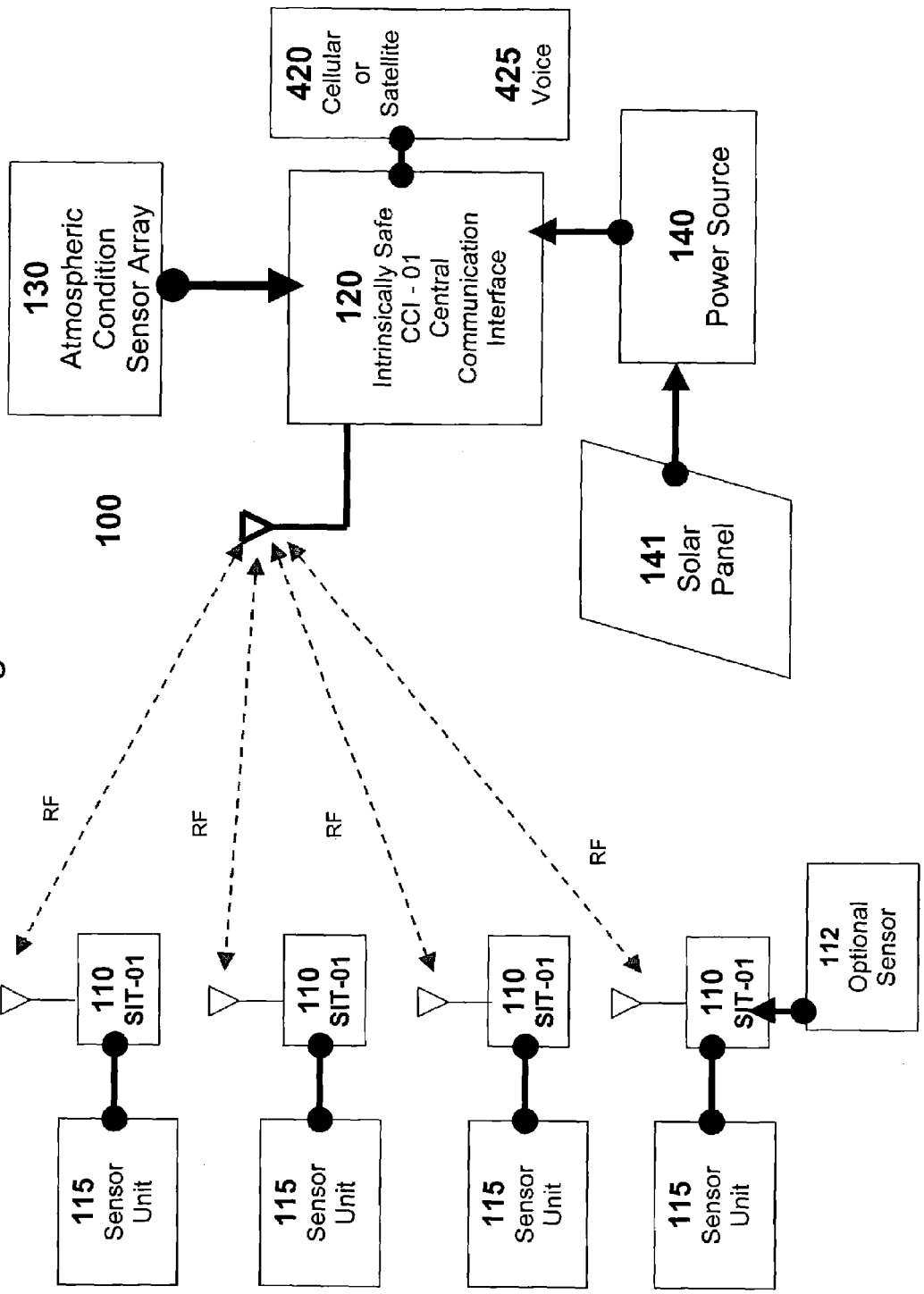
FIG. 1 illustrates one embodiment of the system of the present invention configured for an intrinsically safe on-lease installation at a critical lease.

Referring to FIG. 1 there is illustrated an electronic system including an intrinsically safe Central Communication Interface ("CCI"), multi-mode long-distance communications capability, and a plurality of Sensor Interface Transceivers ("SIT"), together denoted generally as 100, the system 100 being for placement on-site at a critical lease (i.e. hazardous) well site. The CCI element has two configurations being CCI-01 (On Lease) 120 and CCI-02 (Downwind) 220 as set out in FIG. 2. Similarly the SIT element has two configurations being SIT-01 110 and SIT-02 210 as set out in FIG. 2. It is contemplated that the use of a configurable base design for each of the CCI and SIT will lead to manufacturing and production advantages in that the elements of the system of the present invention will be easily substitutable to meet different inventory and operational needs quickly, but affordably.

According to one embodiment, system 100 comprises at least one SIT 110, CCI 120, atmospheric condition sensor array 130, multi-mode long-distance communications apparatus 420, and self-sustaining power source 140 that according to a preferred embodiment is comprised of a battery together with a solar panel 141 and suitable charging circuitry including voltage regulation. Each SIT 110 has at least one sensor unit 115 and accepts at least one optional sensor 112. Each SIT 110 pre-processes (analog or digital) sampled data from sensor units 115 according to programmable circumstances, in a programmable manner, and to a programmable extent in order to ensure that the information required (whether dictated by regulation or otherwise) is available to operators, but without consuming bandwidth unnecessarily. CCI 120 accepts data streams from a plurality of SIT 110 via local (typically low power RF) communication technology and then further processes that data for relay off-site typically using a suitable modem in transceiver that is multi-mode long-distance communications apparatus 420 having access to cellular (CDPD) and satellite transponders over a network. According to one embodiment the selection of CDPD or Satellite communications is (set via DIP switch) made onboard the CCI at the time of installation when the equipment install location is known and confirmed such that it can be determined whether the less expensive cellular communication option is available. However Globalstar technology can also work on CDMA cellular service and kick up to satellite when out of the cellular zone. According to a preferred embodiment the selection of the CDPD or Satellite communication mode is made automatically using optional switch 340 (seen in FIG. 4) that automatically senses the relative signal strength of each said mode determines which to use according to pre-defined rules. As set out in more detail below CCI 120 operates in more than one mode determined by events detected On Lease. In normal operating conditions (i.e. acceptable levels of various gases) sample rates and transmission rates are lower than in emergency or alarm conditions during which data transmissions off-site may be continuous. To reduce the risk that transient conditions at sensor locations will trigger an alarm, according to a preferred embodiment, the processing of CCI 120 includes compensation for atmospheric conditions using data provided by array 130 directly to CCI 120. The housings used in the elements of system 100 are intrinsically safe (e.g. explosion proof) since system 100 must be placed inside critical or "hot" zones On Lease where it provides advantages never before available.

According to one embodiment, system 100 deploys 4 SIT 110 devices each of which receives (analog or digital) data from a third party sensor unit 115 such as the BW Technologies Rig Rat II. Typically each SIT 110 communicates with a single CCI 120 to which it relays the digital form of analog data that the SIT 110 received and converted. All data relays by SIT 110 are wireless RF at any suitable and available frequency, but in one embodiment operate at 900 MHz. CCI 120 performs a variety of processing operations on the data, including accumulation and averaging. According to a further embodiment each SIT 110 may, in either normal or fail-over mode, communicate with more than one CCI 110.

Figure 8:
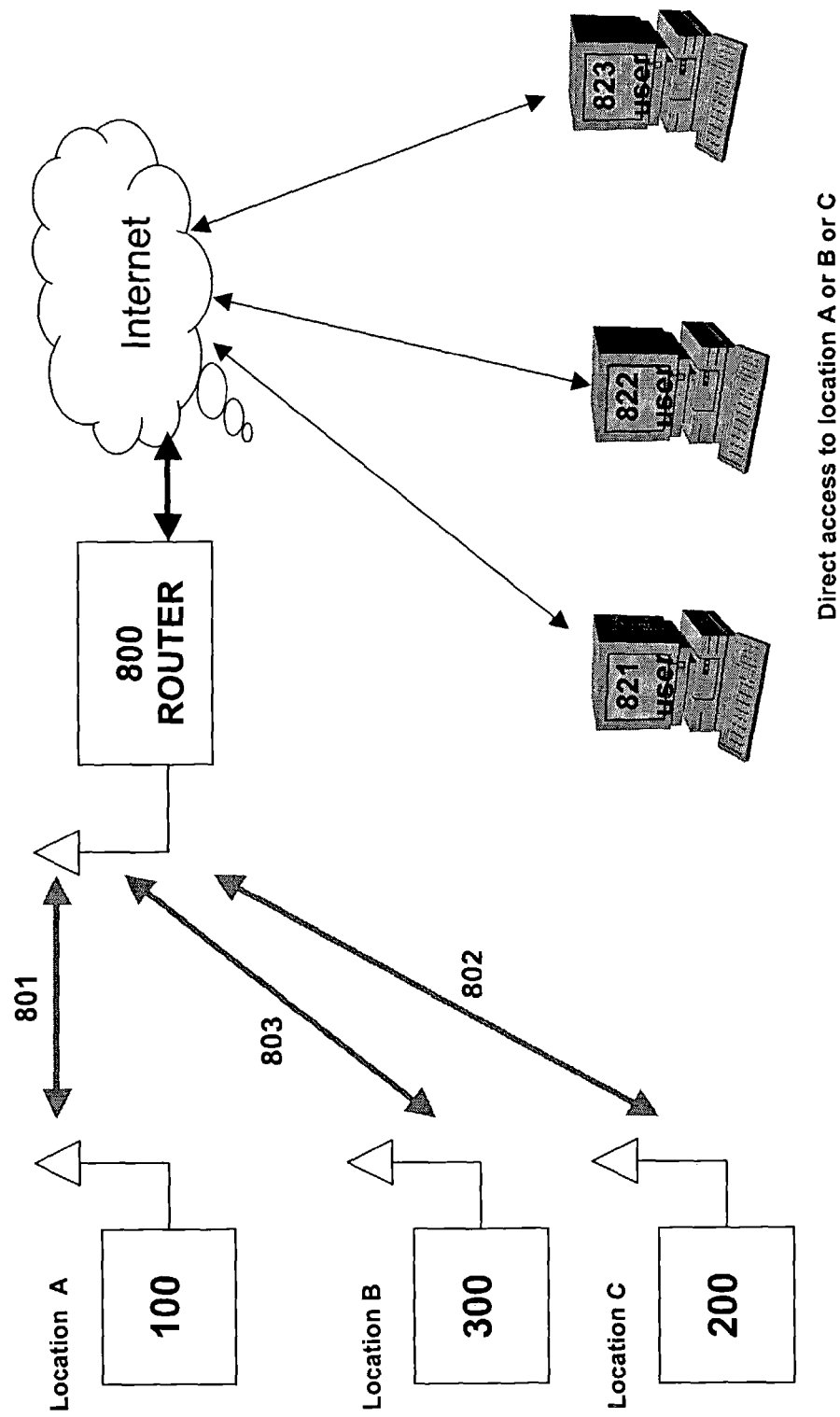
FIG. 8 illustrates one embodiment of the system of the present invention configured in its "server mode" providing data directly to Users.
Figure 9:
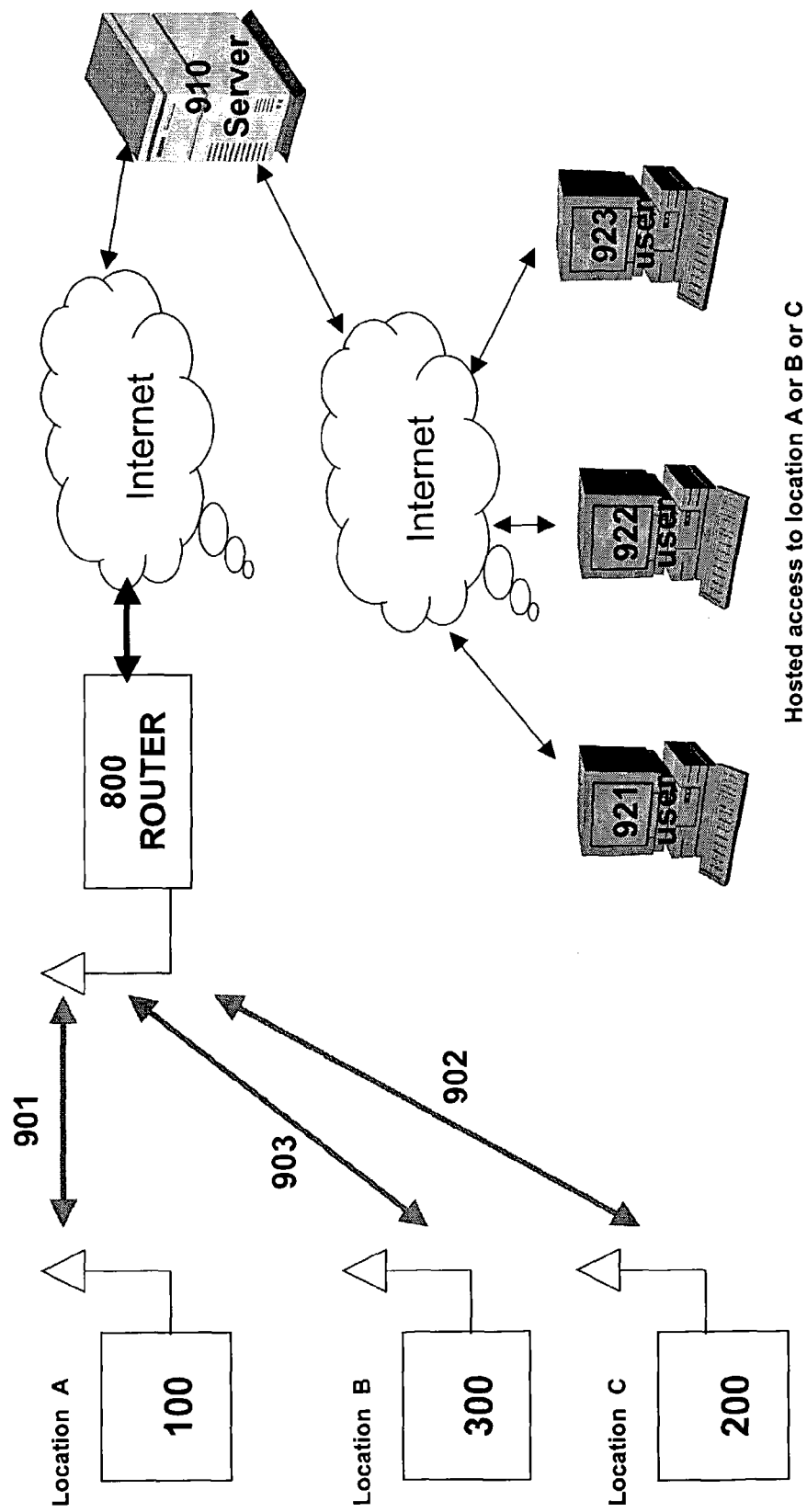
FIG. 9 illustrates one embodiment of the system of the present invention configured in its "client mode" providing data to an external host or server that Users access to reach value-added version of the data from one or more of a plurality of locations.

Each of the two configurations of CCI has at least two modes of operation, normal and alarm. According to a preferred embodiment of CCI 120 operating in normal mode, sample readings are taken every 5 seconds from each SIT 110. Upon accumulating 12 samples (i.e. every 1 minute) from each of the (typically 4) SIT 110 with which it communicates, CCI 120 determines an average for each SIT 110 and records same in Logging Memory 414*b* (seen in FIG. 4). At the same time as logging SIT 110 readings CCI 120 records a variety of atmospheric condition (including, but not limited to temperature and wind speed) readings received from array 130 via interface 415. Typically CCI 120 will have sufficient Logging Memory 414*b* (normally implemented using EEPROM) to accumulate between 2 and 3 hours of data, but in practise CCI 120 may be programmed to transmit all data, thereby clearing its memory registers, every 30 minutes while in normal mode. The accumulation of data is done for economic reasons because the use of satellite means to transmit data remotely is currently relatively expensive. It is contemplated that less or more memory may be used with shorter or longer accumulation periods suited to using CDPD transmission or a smaller client respectively. During transmission CCI 120 sends data in digital format via either CDPD or Satellite means to a remote network that delivers the data to a predetermined IP address from which it may be securely accessed, in client mode or server mode as shown in FIGS. 8 and 9, for a variety of purposes. System 100 uses the data from atmospheric condition sensor array 130 (when CCI 120 processes the gas data that it receives from all SIT 110) to compensate for changes in atmospheric conditions that create spikes or other misleading shifts in the processed gas data. This adjustment advantageously results in fewer anomalous readings in the data that CCI 120 transmits via either cellular or satellite link to a remote monitoring facility or call centre (not shown).

Well site infrastructure is neither required nor relied on with self-sustaining power source 140 used in the On Lease configuration because system 100 operates as an emergency warning system that must continue to operate even if power is lost to the well site—since the loss of well site power would frequently be related to the very type of emergency that system 100 is deployed to detect, monitor, and alert well operators respecting.

To cause it to enter "alarm mode" CCI 120 typically receives an alarm signal via a SIT 110, but generated by a sensor unit 115. CCI 120 may be programmed to react in a variety of ways while in alarm mode, but in a preferred embodiment CCI 120 immediately transmits the contents of its buffer together with a signal generating an e-mail alert to at least one remote monitoring call centre. CCI 120 will typically remain in alarm state until operators intervene to confirm a state of emergency or reset system 100. While in alarm mode CCI 120 typically transmits the contents of its logging memory 414*b* more frequently than in normal mode, but the period between transmissions may be determined by the well site operator based on the nature of the data transmitted, the location of the well site, the cost of transmission, or a variety of other factors. Particularly while connected to a CDPD transmission means, CCI 120 may be remotely caused to transmit the contents of its memory at any time by sending a "request" for the last sample reading. Due to current limitations on satellite technology, while connected to Satellite transmission means, CCI 120 connects to the satellite network according to a pre-programmed schedule, which includes the point at which alarm mode is first entered.

At each of CCI 120 and CCI 220 "data logging" takes place with a plurality of sample reading signals received from each SIT 110 or SIT 210 accumulated over a (programmable) period of time at the end of which the signals are averaged and the average is recorded or "logged" (typically in EEPROM 414*b*) by the CCI 120 or CCI 220 which then accepts a further plurality of signals from each SIT 110 or CCI 210 to create another average for each SIT 110 or SIT 210, each of which averages is again logged. The sequence of accumulation, averaging, and logging for each SIT is repeated continuously until either the expiry of a programmable period of time or an alarm signal is received, upon either of which events the CCI sends data to a modem for transmission to a call centre, where a "library" of the readings from each SIT is created together with date, time, location and any other information useful to the customer operating the monitored well site. The library data may be used in a variety of ways that include the burning of discs of comprehensive record for clients as well as the generation of online graphs that display historical and current levels and trends visually for monitoring.

According to a preferred embodiment of system 100, SIT 110, although capable of accepting raw input from sensor 112, receives its data from a more sophisticated sensor unit 115 such as a gas analyser that detects and measures a wide range of different flammable (LEL %) and noxious gases. Sensor unit 115 will typically provide sufficient electrical power to operate its SIT 110. System 100 is a very bandwidth efficient and cost effective application of technology to prevent a man down scenario while in full compliance with all government regulations. Through 2-way RF communication with sensor units 115, system 100 requires only one modem for a plurality of SMUs (here each comprised of a SIT 110 and at least one sensor unit 115) to implement real time 24/7 monitoring virtually anywhere in the world. By deploying a variety of sensor combinations, system 100 provides early warning of: $H_2S$ ppm, LEL percentages, $H_2S$ ppm; $SO_2$ ppb, as well as security and other threats via event driven JPEG video.

Figure 2:
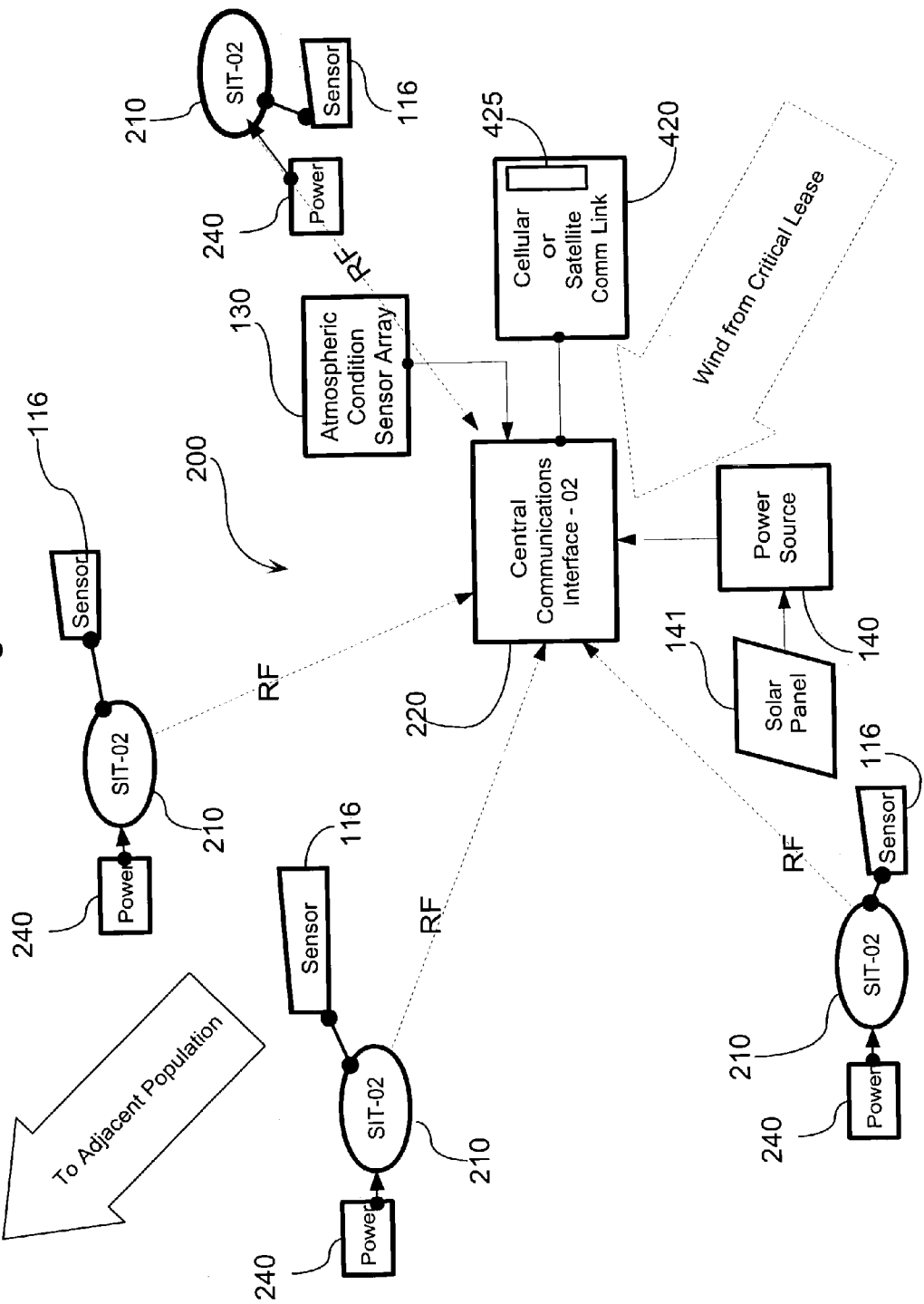
FIG. 2 illustrates one embodiment of the system of the present invention configured for downwind installation.

Referring to FIG. 2 there is illustrated an electronic system, designed to be located downwind from a critical lease well site, and denoted generally as 200. Since system 200 is typically not located inside a hazardous space, government regulations typically do not require that it include intrinsically safe housings on each element. Each system 200 comprises: a CCI 220, at least one SIT 210 each having at least one sensor 116, atmospheric condition sensor array 130, and self-sustaining power sources 140 and 240. System 200 relays data from at least one sensor 116 off site typically using multi-mode long-distance communications apparatus 420. Unlike system 100, system 200 is located remote from any critical or "hot" zones as a result of which system 200 is not exposed to flammable gas while monitoring for $H_2S$ or combustion product $SO_2$. SIT 210 is neither dependent upon (e.g. for power) nor enslaved to an external gas detection and analysis sensor unit 115, such that SIT 210 is connected directly to at least one sensor 116 from which it accepts raw data for processing prior to RF wireless transmission of the processed sensor data to CCI 220 for further processing as required and then remote transmission via cellular (CDPD) or satellite (using multi-mode long-distance communications apparatus 420) to a remote network that delivers the data to a predetermined IP address from which it may be securely accessed for a variety of purposes. Power source 240 is substantially similar to power source 140, (both comprised of a battery together with a solar collector panel and suitable charging circuitry including voltage regulation) however the total output (amp hours) and the solar panel 141 size required to maintain charge on the batteries is matched to the lower power consumption of the SIT 210 as compared to the power consumption of the CCI 120 or the CCI 220.

When CCI 220 processes the data that it receives via RF from each SIT 210 the data from atmospheric condition sensor array 130 is used to compensate for changes in atmospheric conditions that create spikes or other misleading shifts in the processed gas data. Although the placement of each SIT 210 may be dictated by a UTM provided by a government authority, the placement of CCI 220 is determined mainly by the terrain and the range of the particular RF wireless elements used. Typically, with 900 MHz RF communication between it and a CCI 220, each SIT 210 operating as an SMU is located within 1 km of CCI 220. System 200 advantageously requires only a single modem (either Cellular or Satellite) at any time to transfer all the data gathered from a plurality of sensor 116 connected to each of a plurality of SIT 210—providing substantial economy of equipment and communication services costs, as well as reducing the phone numbers and IP addresses that are required to setup and operate conventional downwind technology.

According to a preferred embodiment of systems 100 and 200, CCI 120 and CCI 220 are self-selecting using signal detection and embedded rules to self-select between CDPD and Satellite mode of communication to be used by multimode long-distance communications apparatus 420 at a given location and time as well as in accordance with whether or not the CCI is in normal or alarm mode. Although CDPD is at the time of writing often used for economy, it is contemplated that over time the cost of Satellite communication will decrease and erode the current price advantage of Cellular. Further, particularly as the usage of the once inexpensive CDPD technology increases together with the typical increases in the resulting transmission delays (often due to a higher priority status being granted to more profitable voice traffic) of increased popularity, the selection of satellite mode will be even easier to make for the emergent circumstances normally associated with an alarm condition in the course of monitoring gas wells.

Figure 3:
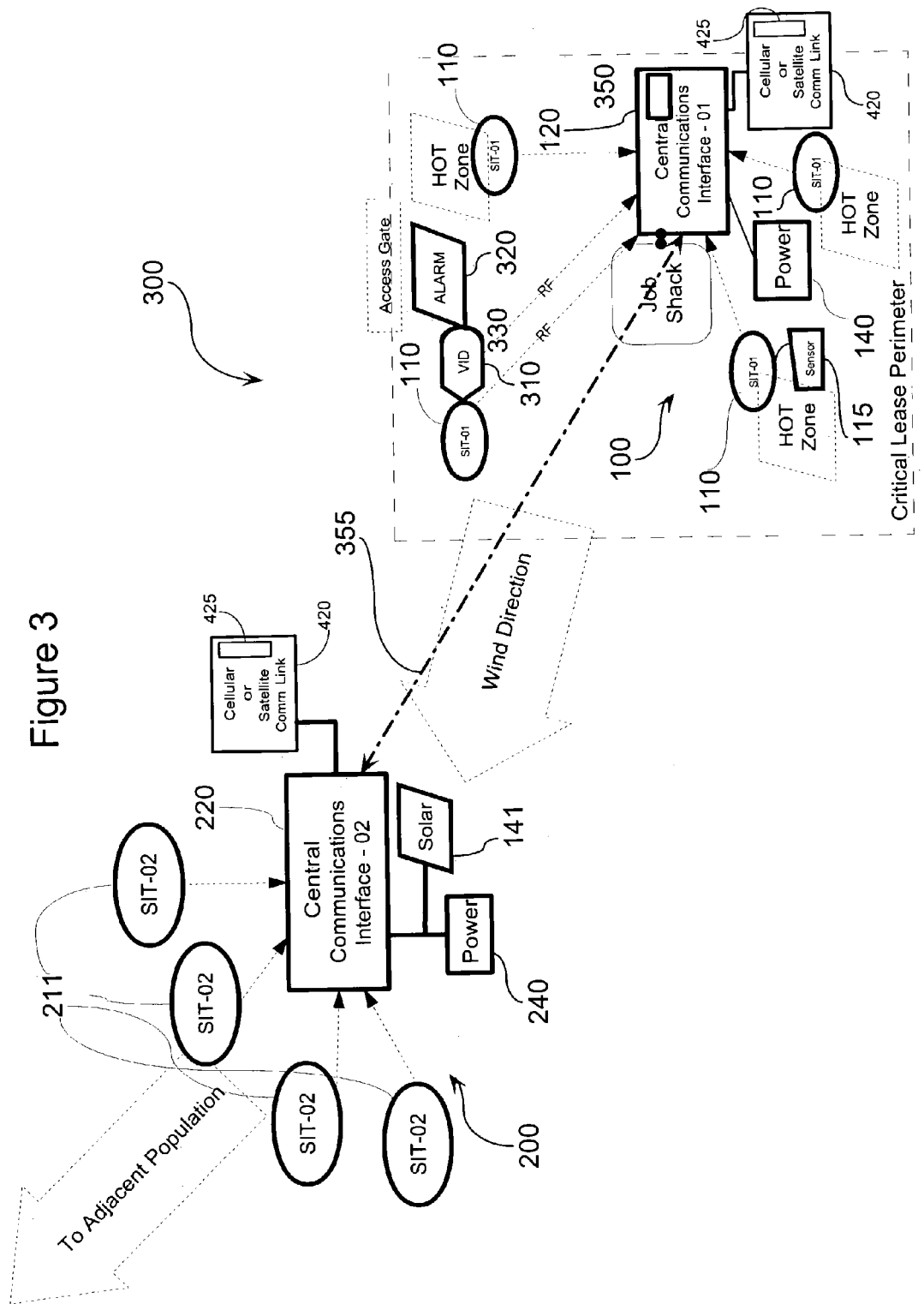
FIG. 3 illustrates one embodiment of the system of the present invention configured for both on-lease and downwind installation.

Referring to FIG. 3 there is illustrated an embodiment of the system of the present invention denoted generally as 300 being the combination of system 100 and system 200. As shown, each subsystem 211 comprises a SIT 210, at least one sensor 116, and a power supply 240. System 300 provides both Downwind and On Lease gas escape detection together with video security respecting a well-site. Each SIT 110 is placed at a location within the critical lease perimeter inside which all equipment must be intrinsically safe to reduce the risk of explosion or fire. Typically, CCI 120 will be located in or near a Job Shack from which site workers operate. In conjunction with system 100 detecting a release of $H_2S$ (for example) gas, system 200 operating downwind provides backup detection and gas cloud movement data. For example, if the third party external gas detection and analysis device, sensor unit 155, supplying data to a SIT 110 downwind of all other devices on lease failed in windy conditions, then any of the 4 independently operating subsystem 211 located downwind could detect the escaped gas and via system 200 alert operators prior to any alarm (local or remote) sounding on lease or generated remotely by any on lease protective system including system 100.

According to a preferred embodiment of system 300, CCI 120 and CCI 220 both cooperate via RF signal 355 and operate as long-distance communications backups to each other. For example, CCI 220 can cooperate with CCI 120 by sampling and transmitting more frequently after receiving an indication from CCI 120 that a gas escape has occurred On Lease. For further example, if either CCI 120 or CCI 220 cannot establish long-distance communications using its own multi-mode long-distance communications apparatus 420, the it may use signal 355 to communicate remotely using the apparatus 420 in the cooperating CCI as a relay. It is contemplated in installations where the SIT 210 downwind sensors are located sufficiently close to the critical lease, that the subsystems 211 may be configured to communicate directly with CCI 120 in order to further economize on equipment and bandwidth.

According to a preferred embodiment, the SMU of at least one SIT is enhanced with VID 310 a security camera, a triggering device ALARM 320, TX 330 a suitable RF transmitter (e.g. the VideoComm line of products), and VIDSERV 350 a suitable video processing and compression device (for example, but not in limitation, the Axis 2400/2401 JPEG video server that typically uses an 8 MB buffer and converts analog video into high quality digital images). Although according to a preferred embodiment VID 310 comprises a very compact CCD colour camera requiring less than 150 ma to operate, a wide range of video or still image devices are suited to this application. Similarly ALARM 320 is typically a motion sensor, a wide range of means of detecting an intruder (human, wildlife, vehicle, aircraft et cetera) approaching or passing through an access point in the critical lease perimeter will detect an event and generate a signal that may be used to trigger VIDSERV 350. In one embodiment VID 310 is supplied with power by the sensor unit 115 or other SMU supporting the SIT. VID 310 runs continuously collecting video images that are RF wirelessly transmitted by signal 330 on a suitable frequency that will not interfere with the RF module in either CCI 120 or CCI 220. VIDSERV 350 continuously receives signal 330 into a buffer that always has the most recent stream of images in storage having overwritten the previous stream. Until an event signal generated by ALARM 320 occurs the CCI operates in normal mode periodically transmitting environmental data, including averaged gas sensor readings. When an event signal is generated by ALARM 320, VIDSERV 350 accesses multi-mode long-distance communications apparatus 420 in a manner that depends on how it has been configured. In a preferred embodiment, when triggered by the event signal of ALARM 320, VIDSERV 350 activates Data Switch 340 (shown in FIG. 4) interrupting access by CCI 120 via Serial Port 416 to take control of apparatus 420 and transmit the processed and compressed video image associated with the triggering event. In an alternate embodiment, VIDSERV 350 communicates through CCI 120 via an RS-232 serial or other suitable port such as either Auxiliary Port 421 or Serial Port 422 and the firmware in 414*a* is programmed to treat signals at the appropriate port as a priority interrupt such that MCU 412 permits the processed and compressed video data stream to access apparatus 420 through Serial Port 416. VIDSERV 350 typically accepts raw video from VID 310 and signal 330, which video is processed to add any identification information (e.g. date, time, and location) required for the particular application and customer installation. In addition to adding required information, the video stream is compressed to any suitable format (e.g. JPEG) prior to being transferred from VIDSERV 350 to apparatus 420. VID 310 may be any suitable camera device but in a preferred embodiment comprises the Optex Wondertrack DC-300 Motion Detector and Camera combined having two relay outputs permitting transmission of signals to both VIDSERV 350 and a well site CCTV recording system. The DC-300 Alarm Output 1 is equipped with a photocell for optional Day/Night operation. The motion detection means typically comprises a passive infrared device, but a wide variety of (flash proof) switches, audio sensors, and similar devices may be used to generate a well site alarm.

According to an alternate embodiment, the transmission device creating signal 330 is not required since VID 310 may be mounted in proximity to VIDSERV 350 permitting a direct wireline connection for high rate data transfer.

ALARM 320 and/or VID 310 may be positioned on lease near access points or targets of concern arising with the presence of protesters, vandals, or terrorists. For example, in a terrorist attack on a gas well site, all the above system configurations work together with each function complementing the others for improved site records. Video devices detect the approach of and potentially provide identification evidence, system 100 provides confirmation of the nature and extent of the gas release associated with the attack, and system 200 provides confirmation of the direction and extent of any resulting release of $H_2S$ in order to facilitate early warning to adjacent land owners.

Figure 10:
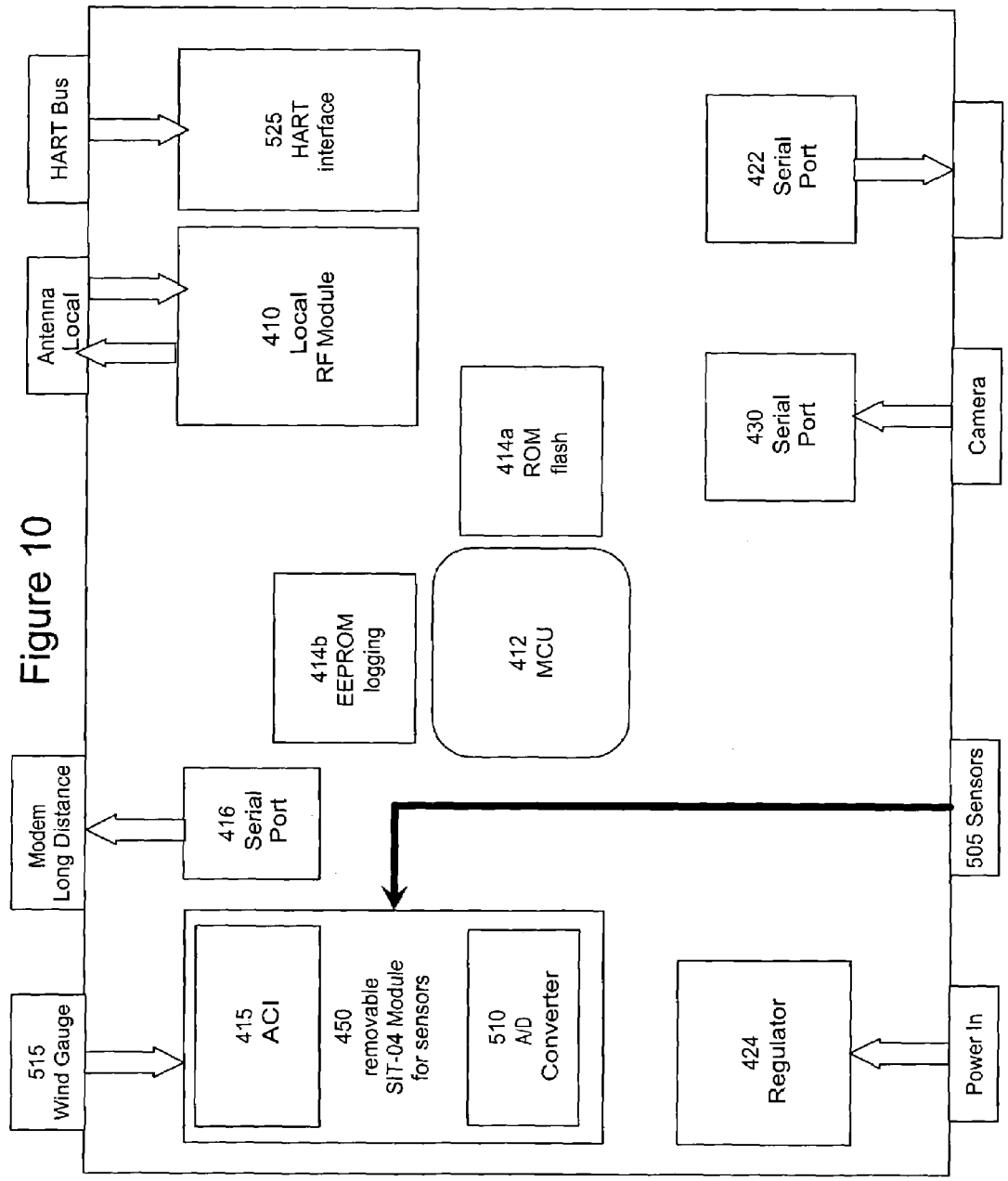
FIG. 10 illustrates in a block diagram one embodiment of the CCI element combined with the SIT element of the system of the present invention.

Referring to FIG. 10 there is illustrated in block diagram form the electronic components of a preferred embodiment of a CCI 120 or CCI 220 having removable sensor module 450 permitting the device to operate as a fully integrated system 100. As an example of the "off the shelf" hardware that may be connected to systems 100, 200, or 300 of the present invention, the HART interface 525 is also illustrated.

Figure 4:
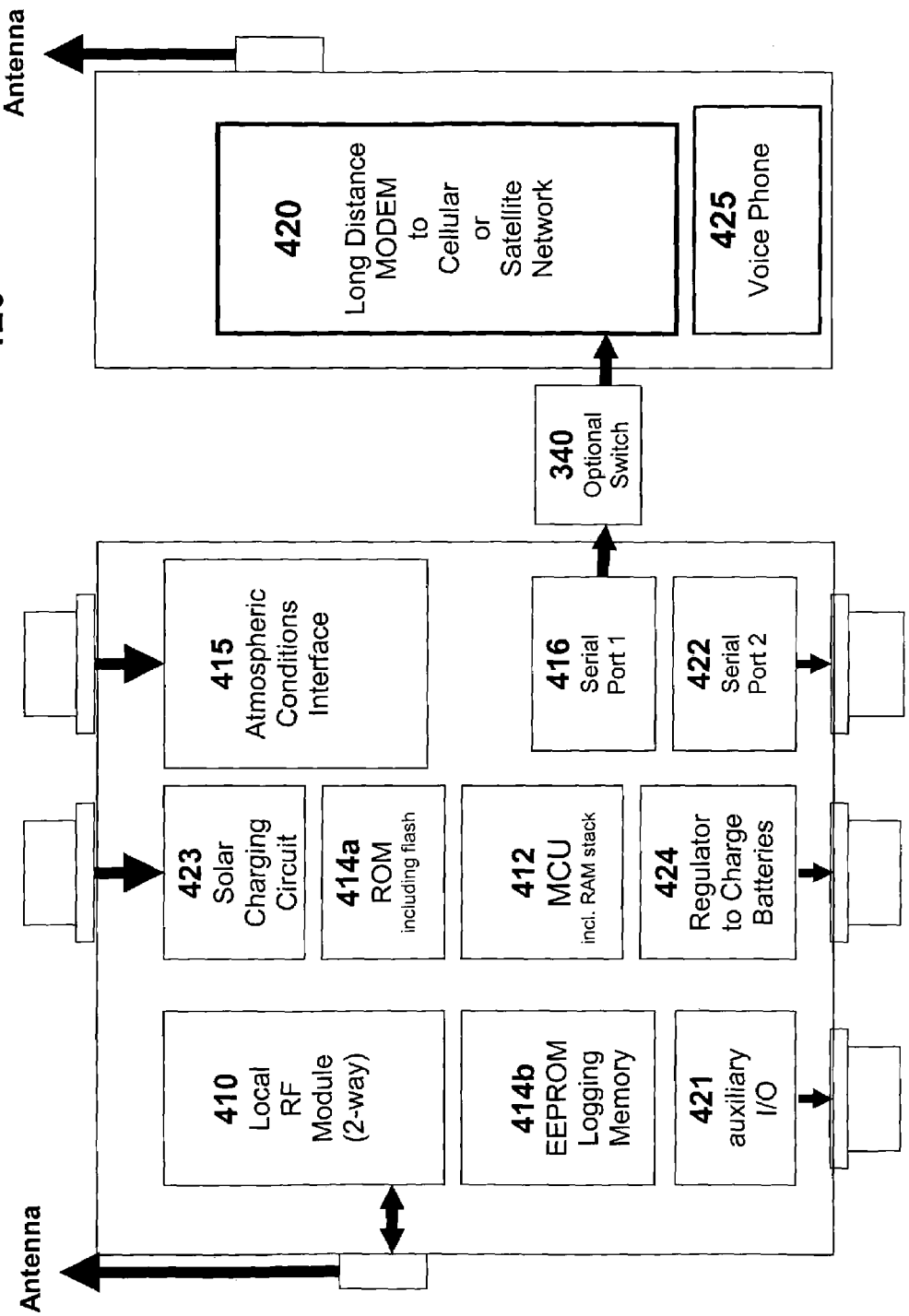
FIG. 4 illustrates in a block diagram one embodiment of the CCI combined with long-distance communication as an element of the system of the present invention.

Referring to FIG. 4 there is illustrated an alternate embodiment of a CCI 120 or CCI 220 wherein local RF Module 410 is used to communicate wirelessly with a SIT (not shown) relaying input data from the sensor unit (not shown) in order to supply data for MCU 412 to process and distribute according to proprietary firmware stored in ROM 414*a* resulting in all conversions and averaging required to interpret the sensor data as well as adjusting the sensor data taking into account atmospheric conditions received through atmospheric conditions interface 415 from array 130. Upon initial processing of a single set of sensor data, EEPROM 414*b* is used to maintain a record thereof in the creation of a data log in which a plurality of sets of sensor data are averaged in accordance with said firmware in ROM 414*a*. Once the data over a programmable period of time is fully processed and adjusted, and the pre-programmed transmit time conditions are met, MCU 412 outputs via serial port 416 to apparatus 420 for transmission using a pre-existing CDPD or satellite network. Auxiliary I/O 421 and Serial Port 422 are both used to enable optional control and interaction alternatives that permit the CCI to be configured for different applications as well as to communicate with other systems and peripherals in the Job Shack. Charging circuit 423 and power Regulator 424 are used to maintain the batteries that supply the CCI.

Advantageously onboard voice phone 425 is provided in the housing of each of elements CCI 120 and CCI 220 in order to reduce the number of telephone devices that operators need to carry for initialization, maintenance, and emergency operation of the system of the present invention. When a system 100, 200, or 300 is installed to monitor well sites not within range of a cellular network the advantage, over conventional systems, of voice phone 425 becomes very significant permitting the operator to verify live readings and conduct tests in real time. According to a preferred embodiment phone 425 efficiently uses the same digital satellite or cellular modem and associated long-distance hardware and carrier account as is used for all environmental data transmissions.

According to a preferred embodiment apparatus 420 comprises a Global Star modem using dynamic IP addressing (to reach the satellite network) for strong data and system security (vs. the less expensive but less secure CDPD cellular network option). Advantageously providing the communication element of system 100 or 200 using a common carrier, such as Global star, which is both voice and data capable reduces the complexity of each system as well as the combined system 300—by operating through a single satellite network to transmit data to an InterNet accessible call center having a fixed IP address, where data is identified, recorded in a library manner, backed up, and available to be redistributed according to the well site operator's needs.

According to a preferred embodiment of the system of the present invention the CCI identifies the "modem of preference" in apparatus 420 using on-board RSSI (relative signal strength indicator) detection means to determine which modem best satisfies the firmware rules in ROM 414a. For example the rules may require for economy that the CCI always use CDPD (cellular) mode if the RSSI is at or above a pre-define transmission strength, but then automatically switch to Satellite mode if the RSSI drops too low to transmit reliably or quickly via CDPD. Further, driven by firmware the CCI may be instructed to continually (e.g. once per second) verify the RSSI level to select the appropriate modem based on specific events (e.g. alarm conditions or standard pre-scheduled delivery of data packets). The CCI housing also typically includes colour-coded LEDs for CDPD (e.g. green) and Satellite (e.g. red) modes in order to permit an operator or service person to determine which modem the CCI has so auto-selected.

According to an alternate embodiment Optional Switch 340 is installed in the communication path, between the serial output from the CCI 120 or CCI 220 motherboard and the apparatus 420, for the purpose of permitting VIDSERV 350 of the optional video security system to temporarily override or interrupt the transfer of environmental data in response to a security alarm event.

Figure 5:
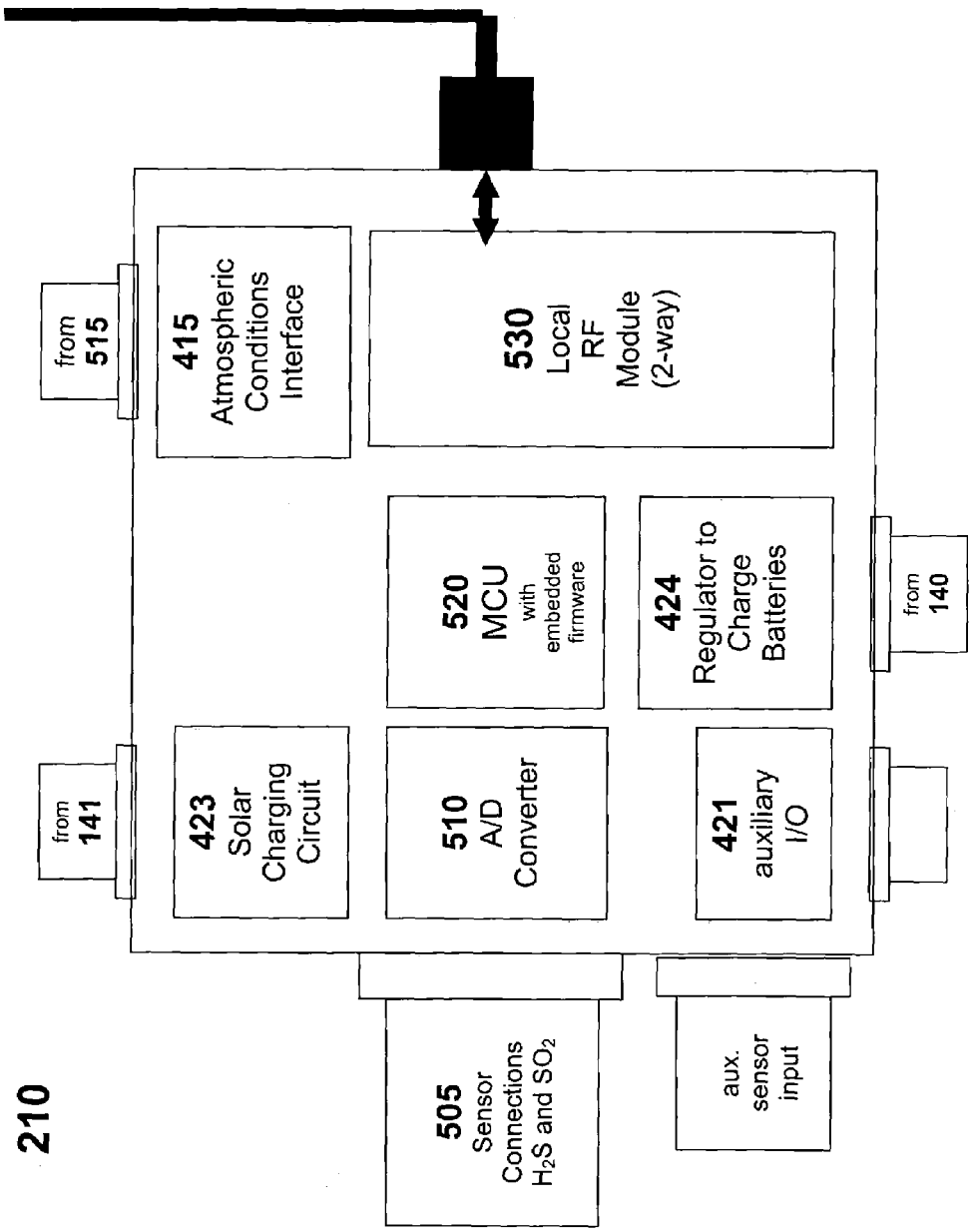
FIG. 5 illustrates in a block diagram one embodiment of the SIT-02 element of the system of the present invention.

Referring to FIG. 5 there is illustrated a block diagram of the SIT 210 element of FIGS. 2 and 3 that provides for the connection of a variety of different sensors (not shown) through port 505, which typically detect the presence of $H_2S$ and $SO_2$. Since SIT 210 accepts unprocessed analog data from a variety of such different sensors, onboard MCU 520 (wherein the processing firmware module is embedded with a RAM stack) is provided with Analog to Digital Converter 510 for the conversion of analog data from all sensor ports. Power Regulation Circuit 424, solar Charging Circuit 423 and auxiliary I/O module 421 are also provided for the supply of power to SIT 210 and to enable a variety of optional access and control features. RF module 530 wirelessly relays the converted sensor data to CCI 220 for further handling. Since SIT 210 is typically deployed spatially isolated from other SIT 210 units in a group, atmospheric conditions interface 415 is advantageously provided in each SIT 210 to permit the detection of a variety of potentially important weather related data over an area of several square kilometers. The weather data is converted to digital form prior to transmission by RF module 530, however it is not normally used by SIT 210 to adjust gas sensor data prior to receipt by CCI 220, wherein the gas sensor data is typically temperature compensated.

Figure 6:
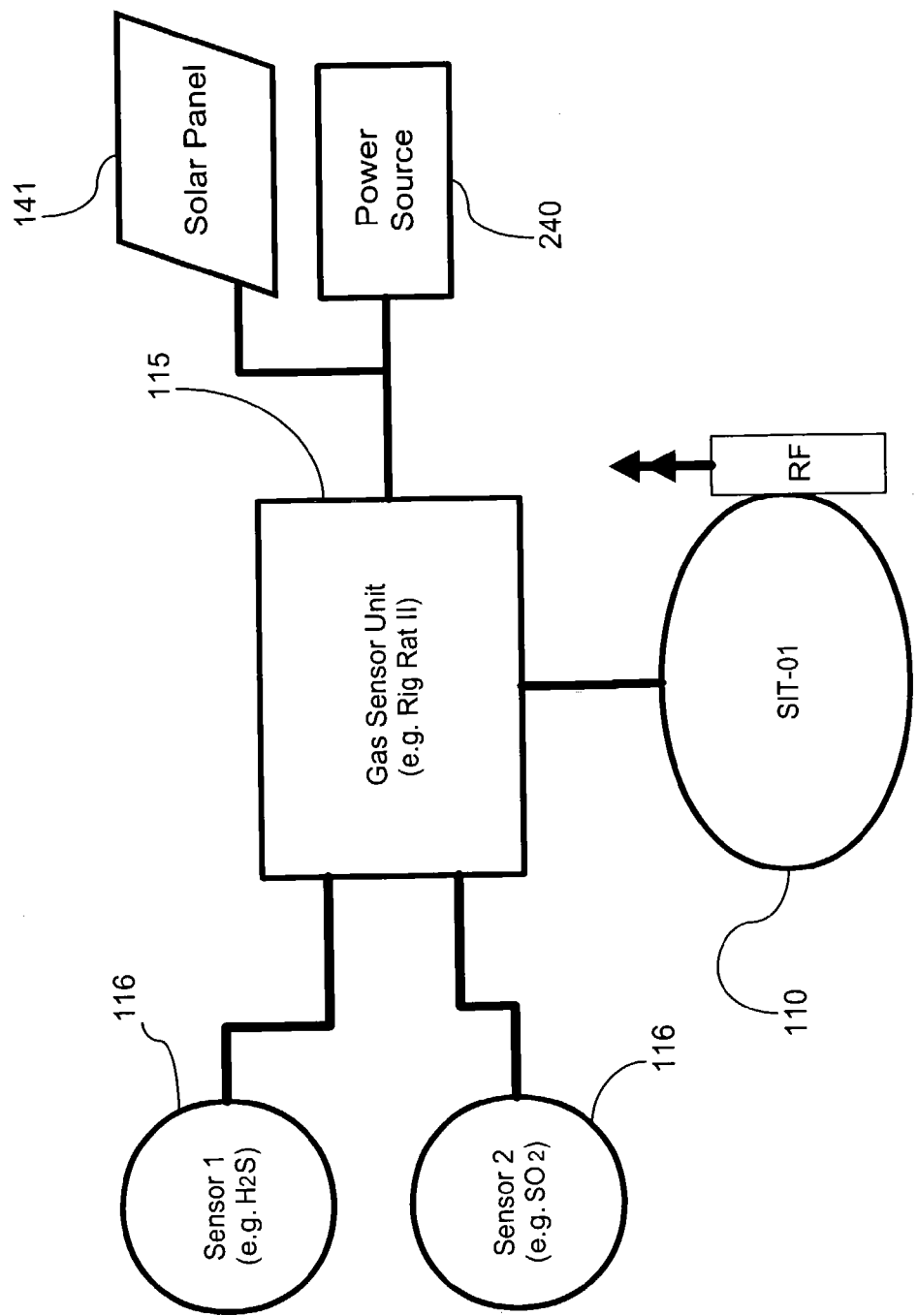
FIG. 6 illustrates one embodiment of the SIT-01 element of the system of the present invention for use as a transmitting relay forwarding data gathered by a third party sensor and logging unit.
Figure 7:
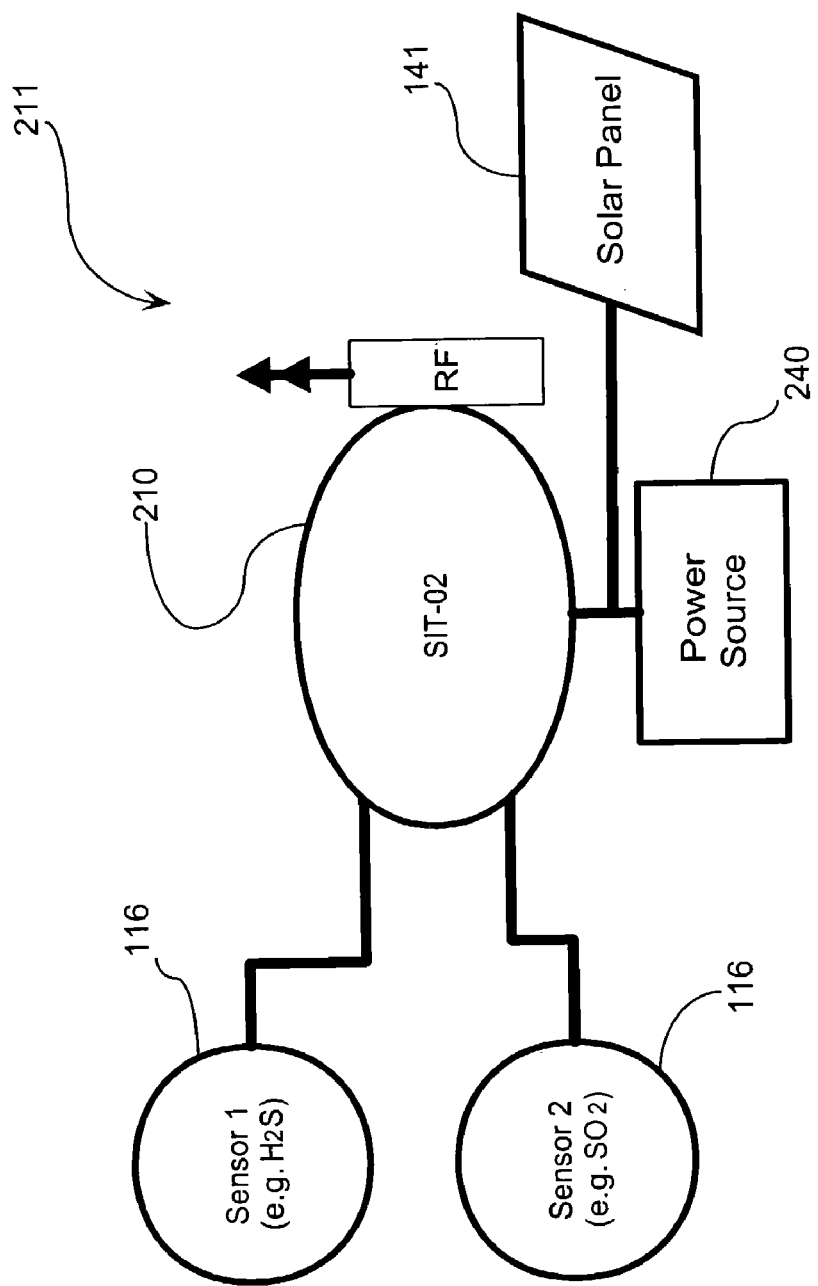
FIG. 7 illustrates one embodiment of the SIT-02 element of the system of the present invention in use with at least one external gas sensing unit from which it processes and forwards data.

The SIT 210 configuration differs from the SIT 110 configuration in that SIT 110 normally operates as a slave to the external sensor unit from which it receives electrical power, whereas the SIT 210 has its own power supply, however the SIT 210 housing need NOT be intrinsically safe since it operates off lease at a downwind location where the risk of reaching the LEL of any flammable gas is negligible. SIT 210 is also configured to accept additional sensor input not required by the SIT 110 configuration that normally receives sensor input from a sophisticated external sensor unit 115, such as is illustrated in FIG. 6 being a block diagram showing SIT 110 in use as a transmitting relay connected to sensor unit 115 being any suitable external gas analyzer. Referring to FIG. 7 there is illustrated a block diagram of an alternate configuration instead showing SIT 210 in use as a detector and transmitting relay connected directly to sensors 116.

Advantageously the system and method of the present invention include and efficiently use an affordable novel combination of known technologies that is useful in a variety of well site monitoring applications that communicate with a remotely located control and monitoring centre using the InterNet.

Referring to FIG. 8 there is illustrated an On Lease system 100 configuration installed at Location A, together with a Downwind system 200 configuration installed at Location C, together with a combined system 300 configuration installed at Location B. The 3 installations communicate wirelessly using one or more routers 800 to reach the Internet. System 100 uses path 801 that may be for example CDPD cellular, while System 300 may be in a more remote location not having cellular infrastructure such that it uses path 803, which may be locked into for example the satellite mode using Global Star, at the same time as System 200 uses an auto-selection, auto-switching mode on path 802 to optimize communication economy as long as the CCI is not in alarm mode. As shown each of the systems is configured in Server mode, such that the CCI of each system "serve their data" directly to operators (e.g. users 821, 822 and 823) requiring a more comprehensive (non-summary) form of record. The "CCI Level" of access available to operators in "Server mode" provides detailed, very current information respecting the gas and other sensor readings at individual SIT 110 and 210 units. Access to the CCI 120 and CCI 220 in Server mode may also be used to "flash" the system (e.g. to reboot the MCU or clear the registers) or to cause the CCI to transmit the contents of its logging memory at virtually any time. It is contemplated that users 821, 822, and 823 may all work for a single larger entity running several locations with different risks, or they may work for different entities each entitled to access to the data for different reasons (e.g. corporate, government watchdogs), or they may work for different companies or venture partners having different access rights to different well sites.

Referring to FIG. 9 there is illustrated, similar to FIG. 8, a group of installations of different embodiments of the system of the present invention capable of cooperating in different ways and for different reasons, but here configured in "Client mode" requiring an external Server permitting end users (customers and operators) 921, 922, and 923 to access a summary of well site data being interpreted, consolidated, and served typically using an Internet web site to display data in a graphic and compact form that is easily understood. Although the user access may for some uses appear substantially similar to that gained under the connections established in FIG. 8, the Server mode lends itself to the use of third party Call Centres that efficiently monitor around the clock more than one well-site for more than one Customer, as well as for easy sharing for regulatory, statistical or other value-added applications of the data available.

The terms and expressions employed in this specification are used as terms of description and not of limitation, and there is no intention in the use of such terms and expressions to exclude any equivalents of the features shown and described or portions thereof, and it is recognized that various modifications are possible within the scope of the invention claimed. Although the disclosure describes and illustrates various embodiments of the invention, it is to be understood that the invention is not limited to these particular embodiments. Many variations and modifications will now occur to those skilled in the art of remote well-site monitoring. For full definition of the scope of the invention, reference is to be made to the appended claims.

We claim:

1. A method to capture and portray information respecting airborne noxious gases present in the atmosphere of or down-wind from a gas or oil production well-site not having access to the communications and power supply public infrastructure typically associated with populated areas, for the purpose of warning remote operators of said well-site of the presence of said gas, the method comprising:

detect, and generate raw data respecting, each said gas present in said atmosphere;

sense atmospheric conditions that cause anomalous readings respecting any said gas so detected;

process said raw data to identify each said gas detected and the concentration thereof so as to generate processed data respecting each said gas present in said atmosphere;

wirelessly communicate locally from a plurality of sensors said raw data or said processed data to a central communication interface operating from an intrinsically safe housing;

create a data log respecting sensor performance or the identity and concentration of said gases;

detect the presence and relative signal strength of any suitable cellular wireless long-distance service, and, based on said signal strength, automatically select between said cellular wireless long-distance means and any suitable satellite transponder long-distance service;

wirelessly transmit long-distance over the Internet said raw data or said processed data, using either said cellular or satellite wireless long-distance service, to a location off-site;

receive said raw data and said processed data at a specified IP address and securely portray through an Internet serving call centre at least a portion of said processed data respecting each said gas identified.

2. The method as claimed in claim 1 further comprising: switch to said satellite service if said cellular service relative signal strength decreases below a pre-defined level.

3. The method as claimed in claim 1 further comprising: capture digital images of activities on or proximal to said remote gas or oil production well-site, and transmit said images over the Internet to said location off-site.

4. A stand-alone electronic warning system to detect airborne noxious gases present in the atmosphere of or down-wind from a gas or oil production well-site not having access to the communications and power supply public infrastructure typically associated with populated areas, for the purpose of warning remote operators of said well-site of the presence of said gas, the system comprising:

at least two sensor means to detect, and generate raw data respecting, each said gas present in said atmosphere;

condition sensing means for sensing atmospheric conditions that cause anomalous output from said sensor means;

processor means, communicably coupled to said sensor means and said condition sensing means, to process said raw data and identify each said gas detected;

a central communication interface, having an intrinsically safe housing, for electronically receiving raw data respecting each said gas from each said sensor, and for electronically receiving processed data from said processor means; wireless local means to communicate said raw data and said processed data to said central communication interface;

a cellular wireless long-distance means, communicably coupled to said central communication interface, for transmitting over the Internet to a location off-site said raw data respecting each said gas detected or said processed data respecting each said gas identified;

a satellite transponder long-distance means, communicably coupled to said central communication interface, and having voice-communication means integrated therein, for transmitting over the Internet to a location off-site said raw data respecting each said gas detected or said processed data respecting each said gas identified;

switching means for selecting either said cellular wireless long-distance means or said satellite transponder long-distance means; and at least one portable source of power for supplying electrical power to each element of said electronic warning system.

5. The system as claimed in claim 4 wherein said cellular wireless long-distance means comprises a modem adaptable to transmitting through a Cellular Digital Packet Data network using Internet protocol via any suitable router or similar device.

6. The system as claimed in claim 4 wherein said satellite transponder long-distance means, having voice-communication means integrated therein, is a Globalstar satellite transponder.

7. The system as claimed in claim 4 wherein said switching means further comprises means for detecting the presence and relative signal strength of said cellular wireless long-distance means, and, based on said signal strength, automatically selecting between said cellular wireless long-distance means and said satellite transponder long-distance means.

8. The system as claimed in claim 4 further comprising any suitable means for storing said raw data or said processed data for the purpose of creating, and maintaining over time, a data log respecting sensor performance or the identity and concentration of said gases.

9. The system as claimed in claim 4 further comprising any suitable camera, video transmitter and video server device, communicably coupled to said central communication interface, for capturing and compressing digital images of activities on or proximal to said remote gas or oil production well-site, for transmitting said digital images over the Internet to a location off-site.

10. The system as claimed in claim 4 wherein said location off-site comprises either: an IP address specified by a user of said system, or an Internet serving call centre for recording, reprocessing, forwarding, viewing, archiving and otherwise handling said processed data respecting each said gas identified.

* * * * *